(12) United States Patent
Becker et al.

(10) Patent No.: US 6,500,199 B1
(45) Date of Patent: Dec. 31, 2002

(54) ENCLOSURE BAG FOR MAINTAINING A PATIENT'S BODY TEMPERATURE DURING SURGICAL PROCEDURES

(76) Inventors: Stephen C. Becker, 9280 N. Lake Dr., Bayside, WI (US) 53217; Michael Bamberger, 9255 N. Pelham Pkwy., Bayside, WI (US) 53217

( * ) Notice: Subject to any disclaimer, the term of this patent is extended or adjusted under 35 U.S.C. 154(b) by 0 days.

(21) Appl. No.: 09/500,613

(22) Filed: Feb. 9, 2000

(51) Int. Cl.⁷ .................................................. A61F 7/00
(52) U.S. Cl. ........................ 607/104; 607/107; 607/109
(58) Field of Search ........................ 607/96, 104, 107, 607/109

(56) References Cited

U.S. PATENT DOCUMENTS

| | | | | |
|---|---|---|---|---|
| 2,416,788 A | * | 3/1947 | Andrews | 34/99 |
| 2,706,988 A | * | 4/1955 | Weber | 128/402 |
| 3,908,655 A | * | 9/1975 | Lund | 128/256 |
| 4,572,188 A | * | 2/1986 | Augustine et al. | 128/380 |
| 5,292,347 A | * | 3/1994 | Pmpei | 607/104 |
| 5,342,411 A | * | 8/1994 | Maxted et al. | 607/107 |
| 5,603,728 A | * | 2/1997 | Pachys | 607/110 |
| 5,609,619 A | * | 3/1997 | Pompei | 607/104 |
| 6,156,059 A | * | 12/2000 | Olofsson | 607/19 |
| 6,228,106 B1 | * | 5/2001 | Simbruner et al. | 607/96 |
| 6,245,094 B1 | * | 6/2001 | Pompei | 607/104 |

\* cited by examiner

Primary Examiner—Linda C. M. Dvorak
Assistant Examiner—Jocelyn Ram
(74) Attorney, Agent, or Firm—Andrus, Sceales, Starke & Sawall, LLP

(57) ABSTRACT

A flexible bag is formed with a opening for placing the bag about the head of the patient and a separate connector for connection to an air supply. The open end has a closure unit permitting the collapse of the opening about the neck to enclose the head. Alternatively, the open end can be placed beneath the ears and over the nose to enclose the upper portion of the head. A separation wall within the bag separates and defines an upper air supply chamber and a lower head heating chamber. The wall has openings including flaps to distribute the air from the air supply chamber to the head enclosing chamber and thereby heating the head with the blood passing therefrom to heat the body of the patient. The head heating chamber includes air directing elements therein. The air supply chamber is L-shaped to direct air over the top of the head and to the side or back of the head. The flexible bag may be formed of a thin plastic and packaged as a flat member with a stack of them provided for single use and throw away as needed in a surgical environment.

7 Claims, 2 Drawing Sheets

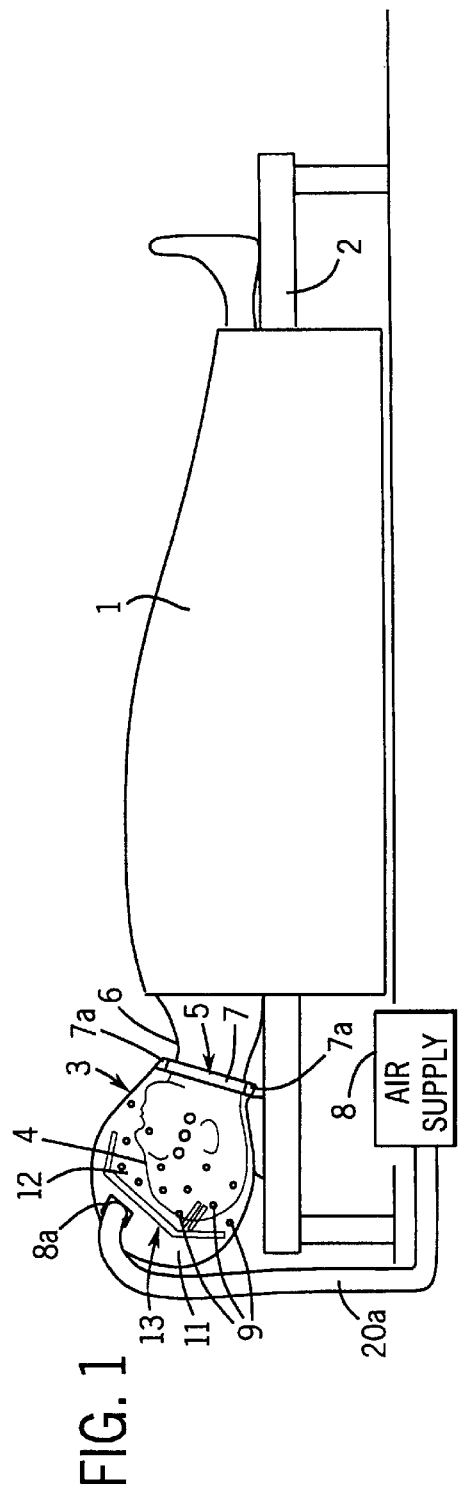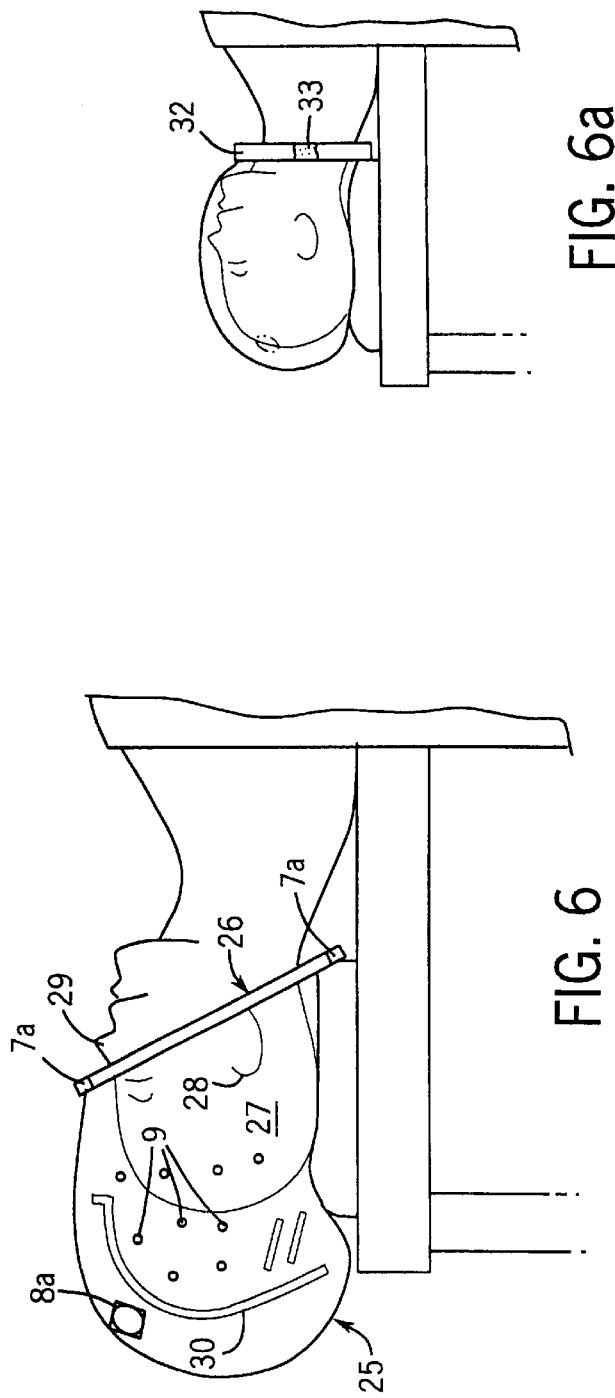
FIG. 1
FIG. 6
FIG. 6a

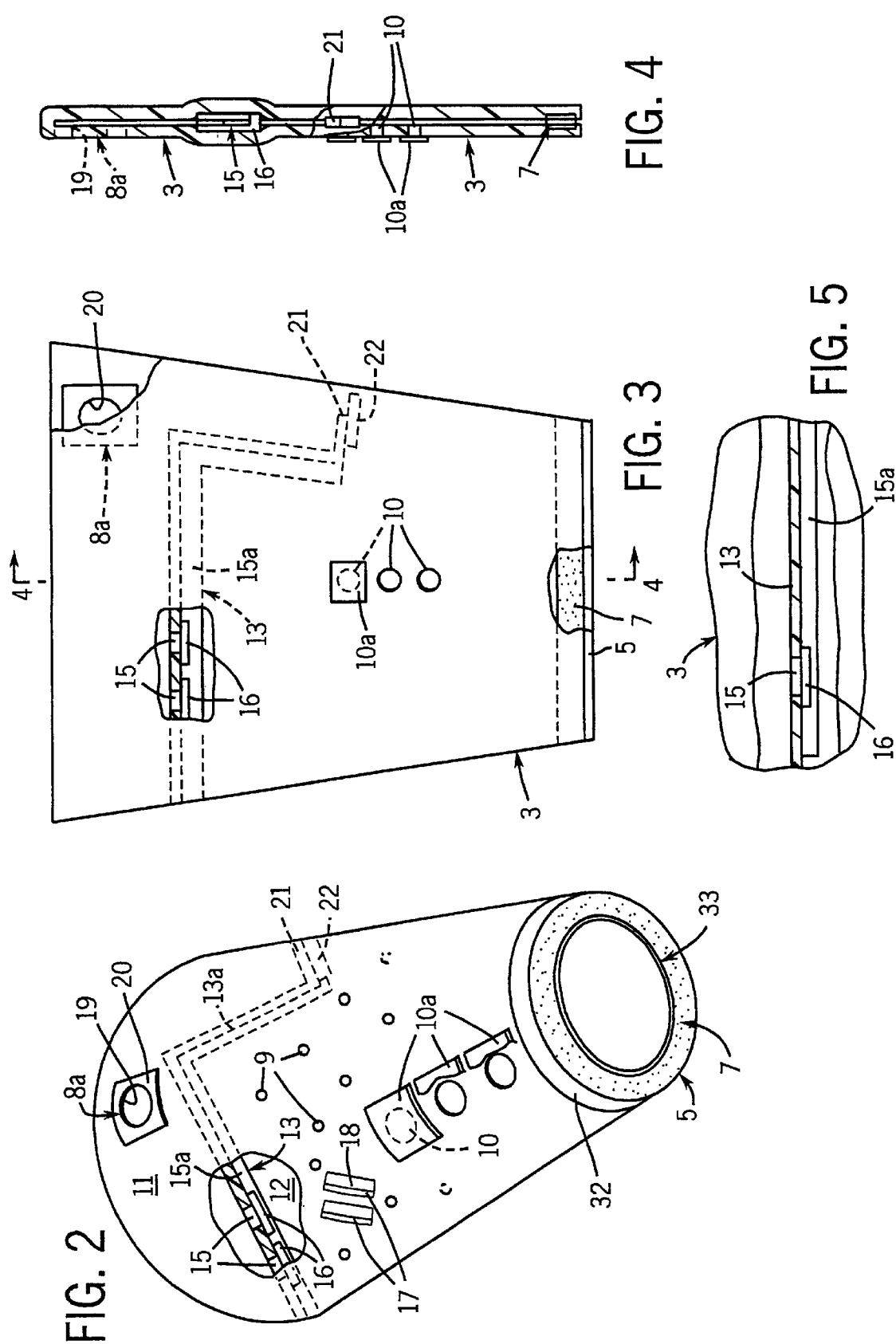

ENCLOSURE BAG FOR MAINTAINING A PATIENT'S BODY TEMPERATURE DURING SURGICAL PROCEDURES

BACKGROUND OF THE INVENTION

A person undergoing surgical procedures advantageously is maintained at a selected temperature by application of external means to prevent body the temperature from dropping below a desired level. Patient heating devices are desirable during surgical procedures as the surgical environment is normally maintained at a relatively cool temperature to aide in the comfort and efficient execution of the surgical procedure by the surgical personnel. Various suggestions have been provided in connection with maintaining the body temperature at a desired warmer level including immersion in a warm bath and alternatively application of body heating elements to the patient's body. U.S. Pat. No. 5,292,347 which issued Mar. 8, 1994 discloses various elements to be applied to the patient's body to supply a heated vapor to the body that lies within an enclosure applied to a particular portion of the patient's body. The system discloses a total body enclosure member and, as an alternative, a cap applied to the top of the patient's head. A non-porous enclosure preferably formed of a thermally insulated material is used so that the heat inside of the closure will not escape. The insulated cover is formed with a condensation accumulating system, and the head unit includes an absorbent material to soak up the condensation. The head structure of the enclosure is also provided with vents to allow excess air and vapor to escape. The system provides a controlled saturated vapor and requires the special body members to appropriately provide the supply of the vapor to the body.

An alternative but similar system is shown in U.S. Pat. No. 4,572,188 which discloses a system including a full body enclosure or a head enclosure with an encircling air band through which air is supplied to surround the head and particularly from the forehead and above. The enclosure pass through a plurality of different passageways and exiting into the body enclosed portion. The structure of U.S. Pat. No. 4,572,188 requires a special air tube which is inflated for sealed engagement with the head in combination with the outer head chamber and extended therefrom. The air is forced within the head band and exits through an outer single port. The tube is specially formed to form insulation and support the head of the patient as well as providing an air passage between the lower portion of the patient's head and the end portion 64. A somewhat similar but cooling device is shown in U.S. Pat. No. 3,908,655 where the patient's head is located within a chamber and an air conditioning applied to provide a cooling of the head directly.

The heating of the patient is preferably through the head portion as a result of the rather great amount of blood which flows through the human head, which when heated will then travel throughout the patient's body at a standard temperature providing an improved heat transfer and distribution. As a result the body is maintained at a comfortable desired temperature throughout the surgical procedure while maintaining a comfortable temperature for medical personnel. This permits optimal efficiency by the surgical personnel. Generally, the patient's temperature will be monitored by skilled personnel during a surgical procedure.

Although the prior art thus recognizes the necessity in various cases to apply air, either thermal or cooling air, to the body to control the temperature during surgical procedures, there remains a need for a very simple and inexpensive single use enclosure unit which can be applied to maintain and control the body temperature during such surgical procedures and thrown away.

In summary, devices have been proposed to enclose the entire head of the person and others to enclose the upper head portion. Separate individual systems have been suggested, but a single relatively simple and inexpensive unit which can be applied in various applications has not been suggested.

SUMMARY OF THE PRESENT INVENTION

The present invention provides a simple and relatively inexpensive flexible enclosure which provides for a single use, throw away usage.

Generally, in accordance with the present invention, a bag unit is provided with an open end in combination with a head enclosure including the open end and an outer air supply chamber. The air supply may be any suitable source of temperature controlled air, and for surgical procedure a supply of heated air. The enclosure bag may be secured with the bag opening secured by various closure elements about the neck portion immediately below the head of the patient, at some further body portion or alternatively above the neck and about a face portion such as beneath the ears and over the nose of the patient to apply the heating effect to the top portion of the head. In each case the bag is preferably formed with appropriate openings for interconnection of appropriate tubing such as for breathing, cleansing and so forth.

In the preferred embodiment, the bag is a simple, biocompatible plastic clear bag which includes an internal separating wall which extends over the top of the head and preferably to one side thereof and defines the air supply chamber to the outer side of the wall and to the other side a head enclosure chamber. The flexible plastic bag is preferably a clear plastic, or at least the frontal part includes a clear portion to allow visual monitoring of the patient. The outer bag wall includes a releasable connection for an air supply tube to receive the heated air. The air is distributed from the supply chamber into the head chamber via the separating wall which is provided with appropriate openings to distribute the air in an optimum manner over and around the head of the patient. The openings may be defined with air directing flaps, and in addition internal walls within the head chamber may be provided to improve the air distribution in accordance with any particular desired configuration.

The bag to be applied to the upper end of the head may be constructed as a smaller unit with a lesser length and have the open end particularly adapted to fitting about the head beneath the ears and over nose portion, or other desired head portions, for firm attachment of the thin flexible cap to the patient's head. The smaller head unit is preferably also provided with appropriate internal separation to produce an air inlet chamber and a head chamber coupled to the face portion to distribute the air in an optimal manner.

The present invention thus provides a very simple and readily constructed flexible bag which can be produced at a relatively low cost and permits the single time usage of the device to maintain the desired maximum sanitary condition required in operating equipment and particularly the equipment used during a surgical procedure.

BRIEF DESCRIPTION OF THE DRAWINGS

The drawings illustrate a best mode presently contemplated of carrying out the invention.

In the drawings:

FIG. 1 is a view of a patient equipped with a bag enclosure illustrating a preferred embodiment of the invention;

FIG. 2 is a pictorial of the bag in fully open state;

FIG. 3 is a front elevational view of the bag in a flat storage position and showing detail of the construction;

FIG. 4 is an enlarged sectional view taken generally on line 4—4 of FIG. 3;

FIG. 5 is an enlarged fragmentary view of the separation wall shown in FIGS. 1–4;

FIG. 6 is a view of the bag applied to the upper head of the patient; and

FIG. 6a is a view illustrating an alternative bag connection.

DETAILED DESCRIPTION OF THE INVENTION

Referring particularly to FIGS. 1 and 2, a patient I is shown supported on a surgical bed 2. The body of patient 1 may be covered with a protective blanket, arranged and constructed for appropriate access to the patient for the surgical procedure. The present invention would be of particular significance where a blanket was not practical, available or the like. An enclosing head bag 3 is shown telescoped over the top of a patient's head 4. The bag 3 includes an open end 5 for placing the bag over the head 4, with the bag open end aligned with and closed about the patient's neck 6. In the illustrated embodiment of the invention, the open end 5 has a closure unit 7, extending completely within the open end 5. When placed on the patient's head, the open end 5 can be collapsed closely about the neck 6 beneath the chin and about the back of the head 4 to define an air chamber surrounding the head. The closure unit 7 is shown for purposed of illustration as a "Velcro" closure unit. Any other suitable closure which will produce at least a reasonably close fit to the aligned part of the body and minimize discharge of air can be used. It is not essential to prevent all air leakage, although such a seal may result. The closure unit 7 is engaged with the excess length, if any, to one or opposite sides of the neck collapsed as at 7a to form a close fit. The closure need not be air tight as air should be released as to establish an outward flow.

An air supply 8 is releasably connected to a air connector 8a in the wall of the bag 3. The bag 3 includes a plurality of distributed pin sized openings 9 to establish at least a minimum flow of air about the head 4 and through the bag. The air supply 8 provides heated air into the bag to maintain the head of the patient in an air temperature of a preselected and preferably controlled minimum temperature. To permit the enclosed attachment to the head, in the illustrated application, the bag is formed with appropriate openings 10 through which tubes can be provided and to attach various parts of the patient for supplying or collecting fluids, air and the like, such as to the patient's nose or mouth for breathing purposes. Three openings 10 are shown for interconnection of auxiliary tubes when required in connection with the comfort and safety of the patient. The openings 10 are closed by releasable covers 10a when not used.

The bag 3 is preferably formed of a relative thin and clear biocompatible thermoplastic material. This permits fill observation of the patient during the procedure. The material also permits the ready construction of the bag at a relatively low material and manufacturing costs. As a result, the bag 3 may be constructed as a throw away and single use product.

The flexible transparent bag 3 provides a very convenient and inexpensive enclosure with continuous visual monitoring of the patient's condition as well as providing a cost effective enclosure structure.

The bag preferably is constructed with a suitable air directing system. In the illustrated and preferred embodiment, a special air input or supply chamber 11 is defined within the upper end and one side portion of the bag and defines a head encircling or enclosing chamber 12 within the bag. An internal separation wall 13 immediately between the chambers 11 and 12 extends across the bag and in the illustrated embodiments, down one side of the bag as at 13a. The wall 13 is located to divide the bag into the upper air inlet and distribution chamber 11 and the side distribution chamber 13a, with the resulting air distributed about the face and side portion of the head 4. The separation wall 13 is thus shown as a generally L-shaped member including a first wall section defining the inlet and distribution portion of the chamber extending across and over the top of the head. The second angled wall portion or section extends downwardly and across a back or side portion of the head to form chamber portion 13a of the chamber 11. The wall 13 is provided with appropriate spaced openings 15 to distribute the air over the head 4 with the air flowing over the head including the face portion to maintain the total body temperature at a reasonable level. Referring particularly to FIGS. 2–5, the dividing wall 13 may be formed as a separate wall secured to the sides of the bag 3 by suitable securement 15a as welds, adhesive or other means. The openings 15 may include control flaps 16 overlying the openings 15 to assist in the distribution of the air from the chamber over the head of the patient. The flaps 16 may be simple plastic members suitably secured adjacent one edge of the opening and opening outwardly in response to the air flow from the supply chamber to the head chamber. In addition, air direction walls 17 within the chamber 13 may be formed by seal lines 18 formed between opposite sides of bag 3 or by a separate wall or walls secured within the bag 3. This allows a more even flow of air and control of the body temperature while maintaining a reasonable comfort level for the patient.

In the illustrated embodiment of the invention, the air connector 8a is located immediately adjacent the uppermost end of the bag and adjacent the one side wall at the junction of the L-shaped chamber 11. It is shown as a supported supply opening 19. Thus, a cardboard or other rigid member is secured to the plastic surrounding the supply opening 19 for receiving of a simple air hose coupling 20 of any suitable and well-known construction connected to an air supply 20a.

The top wall or air supply chamber 11 extends across the width of the bag with outlets or openings 15 generally supplied at the opposite side of the bag. Thus the air flows clear across the bag to the outlets and then drops downwardly about the head of the patient. The angled chamber 13a of the air supply chamber extends along the one side of the bag below the inlet opening 19 and extends approximately one-half the distance to the bottom of the bag and terminates in a small lateral opening 21 equal to about one-half the width of the chamber leg. The opening 21 may include a control flap 22 for distribution of the air.

When the bag 3 is opened and placed on the head of the patient, it encircles the head with the extended passageways across the top of the head and also down along one side of the head, with the lateral opening 21 located generally in the area of the nose and mouth of the patient.

Although the structure of the inner passageway and the outlet is not critical, it is desirable to provide an appropriate location of the bag unit to maintain the maximum comfort to the patient.

The illustrated bag is a particularly simple, reliable and inexpensive heating enclosure readily adapted for surgical procedures. The transparent bag provides continuous monitoring of the condition of the patient by the operating personnel as well as providing the necessary connections to the patient for breathing and the like.

In certain procedures, it may be desirable to merely place an enclosure about the upper portion of the patient's head thus leaving the lower extremity of the head beneath the nose essentially exposed. A bag 25 is shown in FIG. 6 of the construction of bag 3. In this particular application, the open end 26 encircles the upper end of the head 27. The open end 26 is shown passing beneath the ears 28 and above the nose 29. The open end is closed about the encircled upper portion of the head. The closure maintains a more or less substantially closed air chamber about the top of the head. Any opening about the nose, ears or other parts of the head do not significantly affect the desired air flow.

The bag 25 is otherwise similarly constructed to that of bag 3, and in fact may be of the identical construction. The bag 25 may however also be smaller but otherwise is preferably essentially similarly constructed. Thus it preferably includes the generally L-shaped supply chamber 30 extending across the upper portion of the bag and an extended side chamber extending downwardly to the terminating upwardly spaced relation to the bottom securing end of the bag.

The location in FIG. 3 is illustrative of a particularly satisfactory system. Other variations may be used, such as, over the ears and beneath the nose or simply around the head at or below the nose and/or mouth, with the bag provided with the separate openings if necessary because of the covering of the nose, mouth or the like.

The bags 3 and 25 are shown formed with the dividing walls formed by separate elements secured within and to the bag walls as joining the opposed walls of the bag. The separating walls may be formed by heating of the bags, by the use of suitable adhesive or any other means of joining the bag to form the dividing walls. The dividing walls may include spaced opening for placing the air into the head chamber.

The closure 33 may include a foam member 32 (FIG. 6a) to be wrapped about the patient at the bag attachment location with a closure unit 32 placed over the foam member 32. The closure 33 is closed to partially compress the aligned foam member. As shown in FIG. 6a, this will provide a firm and comfortable attachment while permitting a bag with a relatively larger end opening to fit the bag to the patient, with the head, neck and/or other body portion of different sizes.

The illustrated bag is readily formed of a thin plastic which is suitable for use in a surgical environment. A plastic material which has been used is resin with copolymer additives. The flexible bag is preferably a relatively thin unit and may be readily formed (as shown in FIGS. 3–6a) as a flat bag for assembly and storage in a convenient package for use as individual bags as needed.

Further, although shown with the particular dividing walls and openings, other embodiments may be readily formed depending on the various specification and requirements. The separations of the chamber may, for example, be formed by sealing of the opposed wall sections to form a multiple several chamber enclosure, with the seal lines having the desired openings for air transfer. Similarly, the open end may be provided with any other desired manually set closure such as a releasable line unit, slot and projection member or others which permit the enclosure with a reasonable fit to the patient's body.

The above embodiments disclose preferred and unique embodiments for a one-time use in a body temperature head enclosure. The enclosure may be formed as a simple single chamber flexible bag with at least one attachment opening for attachment to enclose the head, totally or in part. The transparent bag with the special heated air supply chamber and an air distribution system built within the bag provides a more reliable and effective system. Although shown in the preferred construction as formed from a single bag, the bag may be formed from separate bags having common connected walls to define the separating walls. The bag may be formed with other chambers for location with respect to particular portions of the patient to be covered with an air flow. Thus, the invention is particularly directed to the use of a flexible bag element, preferably incorporating the wall to form the two separate chambers. As defined in the claims, a bag will include the above variations as well as others providing a structure functioning as disclosed in the illustrated embodiment and discussed herein. Further, although a clear bag formed of single material is preferred, other bags material may be used but should provide for visual monitoring of the patient's face in order to maintain a most safe procedure.

We claim:

1. A surgical, disposable plastic bag for providing heated air from a heated air supply for use in supplying heated air onto and over the head of a patient for controlling the temperature of the head of the patient and thereby the temperature of the patient's body during a surgical procedure, comprising a flexible thin and transparent bag having an attachment opening configured for fitting of the bag over the head of the person with the opening aligned with a portion of the person's body, said bag opening including a closure structure to close the opening at the body and define an enclosure encircling at least the upper head of the patient, said bag having an air inlet configured for connection to a heated air supply to supply heated air into the bags, an internal dividing wall dividing the bag into an air supply chamber including said air inlet for receiving said heated air and a head enclosing chamber in said bag including said internal dividing wall and enclosing at least the upper head of said patient, said dividing wall including openings for directing of the air onto said head within said head enclosing chamber and thereby maintaining a heated air environment within the bag for heating of the head and controlling the temperature of the patient's body during the surgical procedure, and wherein said dividing wall is spaced upwardly from said at least one attachment opening to form a top air supply chamber, said air supply chamber having an offset leg extending from said top air supply chamber downwardly across a side of said bag to form a side air supply chamber and having outlet openings in both of said side air supply chamber and top air supply chamber for distributing of the air about the enclosed head portion of the patient.

2. A surgical, disposable plastic bag for providing heated air from a heated air supply for use in supplying heated air onto and over the head of a patient for controlling the temperature of the head of the patient and thereby the temperature of the patient's body during a surgical procedure, comprising a flexible thin and transparent bag having an attachment opening configured for fitting of the bag over the head of the person with the opening aligned with a portion of the person's body, said bag opening including a closure structure to close the opening at the body and define an enclosure encircling at least the upper head of the patient, said bag having an air inlet configured for connection to a heated air supply to supply heated air into the bags, an internal dividing wall dividing the bag into an air supply chamber including said air inlet for receiving said heated air and a head enclosing chamber in said bag including said internal dividing wall and enclosing at least the upper head of said patient, said dividing wall including openings for directing of the air onto said head within said head enclosing chamber and thereby maintaining a heated air environment within the bag for heating of the head and controlling the temperature of the patient's body during the surgical procedure, and having internal air deflection walls formed within the head enclosure chamber.

3. A surgical, disposable plastic bag for providing heated air from a heated air supply for use in supplying heated air onto and over the head of a patient for controlling the temperature of the head of the patient and thereby the temperature of the patient's body during a surgical procedure, comprising a flexible thin and transparent bag having an attachment opening configured for fitting of the bag over the head of the person with the opening aligned with a portion of the person's body, said bag opening including a closure structure to close the opening at the body and define an enclosure encircling at least the upper head of the patient, said bag having an air inlet configured for connection to a heated air supply to supply heated air into the bags, an internal dividing wall dividing the bag into an air supply chamber including said air inlet for receiving said heated air and a head enclosing chamber in said bag including said internal dividing wall and enclosing at least the upper head of said patient, said dividing wall including openings for directing of the air onto said head within said head enclosing chamber and thereby maintaining a heated air environment within the bag for heating of the head and controlling the temperature of the patient's body during the surgical procedure, and wherein said dividing wall being substantially L-shaped with one leg extended across the bag to form a supply chamber above the head and a second leg extended along a side of the head enclosing chamber to form a supply chamber adjacent the side of the head, each of said legs having said openings directing air into the head enclosure chamber.

4. The bag of claim 3 wherein closure flaps are secured to the dividing wall to cover said openings and are moved to open the openings in response to the air pressure within said legs of said dividing wall.

5. A surgical, disposable plastic bag for providing heated air from a heated air supply for use in supplying heated air onto and over the head of a patient for controlling the temperature of the head of the patient and thereby the temperature of the patient's body during a surgical procedure, comprising a flexible thin and transparent bag having an attachment opening configured for fitting of the bag over the head of the person with the opening aligned with a portion of the person's body, said bag opening including a closure structure to close the opening at the body and define an enclosure encircling at least the upper head of the patient, said bag having an air inlet configured for connection to a heated air supply to supply heated air into the bags, an internal dividing wall dividing the bag into an air supply chamber including said air inlet for receiving said heated air and a head enclosing chamber in said bag including said internal dividing wall and enclosing at least the upper head of said patient, said dividing wall including openings for directing of the air onto said head within said head enclosing chamber and thereby maintaining a heated air environment within the bag for heating of the head and controlling the temperature of the patient's body during the surgical procedure, and wherein said bag is formed of a biocompatible plastic, and wherein said plastic includes clear plastic at least in a portion of the bag for alignment with the face of the patient, and wherein said bag includes at least one opening configured to receive treatment tubing required for coupling to the various parts of the head of the patient during a surgical procedure; and said bag having said air inlet unit adjacent a closed end of the bag for releasably receiving an air supply for admitting temperature controlled air into the bag for inflating the bag and supplying a heated air to maintain the head of the patient in a heated condition suitable for application to the patient during-the surgical procedure.

6. A surgical, disposable bag for delivering heated air to the head of a patient for controlling the temperature of the head and thereby the body of the patient during a surgical procedure, comprising:

a flexible bag formed having an open end configured and constructed for fitting of the bag over the head of the person with the open end aligned with a particular portion of the person to enclose at least an upper portion of the head, said bag having at least a clear portion configured to provide visual appearance of the face of the patient, said flexible bag having an air inlet unit formed in the upper closed end of the bag, and a separation wall within said bag defining an air supply chamber adjacent the closed end of the bag and a head heating chamber to the opposite side of said separation wall, said separation wall having a plurality of openings extended across the separation wall for directing of air from said supply chamber to the opposite side of said separation wall into said head heating chamber and onto the head and thereby supplying heated air onto and about the head of the patient for at least assisting in controlling the temperature of the body of the patient, and having air deflecting members within said heating chamber.

7. A surgical, disposable bag for delivering heated air to the head of a patient for controlling the temperature of the head and thereby the body of the patient during a surgical procedure, comprising:

a flexible bag formed having an open end configured and constructed for fitting of the bag over the head of the person with the open end aligned with a particular portion of the person to enclose at least an upper portion of the head, said bag having at least a clear portion configured to provide visual appearance of the face of the patient, said flexible bag having an air inlet unit formed in the upper closed end of the bag, and a separation wall within said bag defining an air supply chamber adjacent the closed end of the bag and a head heating chamber to the opposite side of said separation wall, said separation wall having a plurality of openings extended across the separation wall for directing of air from said supply chamber to the opposite side of said separation wall into said head heating chamber and onto the head and thereby supplying heated air onto and about the head of the patient for at least assisting in controlling the temperature of the body of the patient;

wherein said bag includes at least one opening configured to receive treatment tubing required for coupling to the various parts of the head of the patient during a surgical procedure; and said bag having said air inlet unit adjacent the closed end of the bag for releasably receiving an air supply for admitting temperature controlled air into the bag for inflating the bag and supplying a heated air to maintain the head of the patient in a heated condition suitable for application to the patient during the surgical procedure.

* * * * *